US008361504B2

(12) United States Patent
Hen et al.

(10) Patent No.: US 8,361,504 B2
(45) Date of Patent: Jan. 29, 2013

(54) MATERIALS AND METHODS FOR WOUND TREATMENT

(75) Inventors: John Hen, Bradenton, FL (US); John Alfred Thompson, Nassau (BS); Talmadge Kelly Keene, Apollo Beach, FL (US); Michael H. Tollon, Largo, FL (US); Mark Travi, Sarasota, FL (US); Roger Thomas, Pinehurst, NC (US)

(73) Assignee: Biolife, LLC, Sarasota, FL (US)

( * ) Notice: Subject to any disclaimer, the term of this patent is extended or adjusted under 35 U.S.C. 154(b) by 34 days.

(21) Appl. No.: 12/421,300

(22) Filed: Apr. 9, 2009

(65) Prior Publication Data
US 2009/0252799 A1 Oct. 8, 2009

Related U.S. Application Data

(63) Continuation-in-part of application No. PCT/US2007/021782, filed on Oct. 11, 2007.

(60) Provisional application No. 60/850,932, filed on Oct. 11, 2006.

(51) Int. Cl.
*A61K 9/14* (2006.01)
*A61K 33/26* (2006.01)
*A61L 15/00* (2006.01)

(52) U.S. Cl. ......... 424/486; 424/647; 424/646; 424/445

(58) Field of Classification Search .................. 424/486, 424/647, 400, 646, 445; 521/143
See application file for complete search history.

(56) References Cited

U.S. PATENT DOCUMENTS

| | | | |
|---|---|---|---|
| 3,669,103 A | 6/1972 | Harper et al. | |
| 3,670,731 A | 6/1972 | Harmon | |
| 4,654,039 A | 3/1987 | Brandt et al. | |
| RE32,649 E | 4/1988 | Brandt et al. | |
| 5,461,085 A | 10/1995 | Nagatomo et al. | |
| 5,525,703 A | 6/1996 | Kalota | |
| 5,612,384 A | 3/1997 | Ross et al. | |
| 5,750,585 A * | 5/1998 | Park et al. | 521/143 |
| 6,187,347 B1 * | 2/2001 | Patterson et al. | 424/646 |
| 6,238,691 B1 | 5/2001 | Huang et al. | |
| 6,271,278 B1 | 8/2001 | Park et al. | |
| 6,326,410 B1 | 12/2001 | Cheong et al. | |
| 6,399,092 B1 | 6/2002 | Hobson et al. | |
| 6,500,539 B1 | 12/2002 | Chen et al. | |
| 6,787,682 B2 | 9/2004 | Gilman et al. | |
| 6,861,067 B2 | 3/2005 | McGhee et al. | |
| 6,936,746 B2 | 8/2005 | Effing et al. | |
| 6,960,617 B2 | 11/2005 | Omidian et al. | |
| 7,056,957 B2 | 6/2006 | Omidian et al. | |
| 2001/0038831 A1 | 11/2001 | Park et al. | |
| 2002/0197302 A1 * | 12/2002 | Cochrum et al. | 424/445 |
| 2003/0008007 A1 | 1/2003 | Gutierrez-Rocca et al. | |
| 2003/0008011 A1 | 1/2003 | Mershon | |
| 2003/0232895 A1 | 12/2003 | Omidian et al. | |
| 2004/0224021 A1 | 11/2004 | Omidian et al. | |
| 2005/0137512 A1 | 6/2005 | Campbell et al. | |

FOREIGN PATENT DOCUMENTS

| | | |
|---|---|---|
| EP | 0312952 A2 | 4/1989 |
| EP | 0441507 A1 | 8/1991 |

OTHER PUBLICATIONS

Gooch, Barrier Dressings for Wounds, Chapter 2 of Biocompatible Polymeric Materials and Tourniquets for Wounds, Aug. 15, 2006, pp. 7-71.*
Dorkoosh, F.A. et al., "Evaluation of superporous hydrogel (SPH) and SPHcomposite in porcine intestine ex-vivo: assessment of drug transport, morphology effect, and mechanical fixation to intestinal wall", *Eur J Pharm Biopharm*, 2002, 53:161-166.
Park, K., "Superporous Hydrogels for Pharmaceutical & Other Applications", *Drug Delivery Technologies*, Jul./Aug. 2002, 2(5):1-9.
Chen et al. "Synthesis of superporous hydrogels: Hydrogels with fast swelling and superabsorbent properties", *Journal of Biomedical Materials Research*, 1999, 44:53-62.
Wichterle et al. "Hydrophilic Gels for Biological Use", *Nature*, 1960, 185:117-118.
Chen et al. "Gastric retention properties of superporous hydrogel composites", *J. Controlled Rel.*, 2000, 64:39-51.
Shalaby et al. "Use of ultrasound imaging and fluoroscopic imaging to study gastric retention of enzyme-digestible hydrogels", *Biomaterials*, 1992, 13:289-296, abstract only.
Dorkoosh, F.A. et al. "Development and characterization of a novel peroral peptide drug delivery system", *J. Controlled Rel.*, 2001, 71:307-318.
Chang et al. "Fast—Dissolving Tablets" *Pharm Technol.*, 2000, 24(6):52.

* cited by examiner

*Primary Examiner* — Blessing Fubara
(74) *Attorney, Agent, or Firm* — Saliwanchik, Lloyd & Eisenschenk; Doran R. Pace

(57) ABSTRACT

The subject invention pertains to materials and methods for stopping or decreasing the blood flow from an open wound or medical or surgical procedure. Compositions of the invention comprise a salt form of a cross-linked polyacrylic acid. In one embodiment, the composition comprises a sodium salt of a polyacrylic acid. Compositions of the invention can also optionally comprise one or more different salt ferrates, and/or a cationic exchanger resins, and/or a silver compound. In an exemplified embodiment, a composition of the invention comprises sodium polyacrylate provided in a dry powdered form. Polyacrylate compositions of the invention can be applied directly to a wound or treatment site, or they can be incorporated into a wound dressing, such as a bandage. The clot or scab formed at a wound or treatment site treated with the present invention is extremely elastic and exhibits considerable tensile strength when stretched to the breaking point. The subject invention also concerns wound and surgical site dressings and coverings, and methods of using a composition of the invention to stop blood flow from an open wound or treatment site.

29 Claims, 1 Drawing Sheet

MATERIALS AND METHODS FOR WOUND TREATMENT

CROSS-REFERENCE TO RELATED APPLICATION

This application is a continuation-in-part of International Application No. PCT/US2007/021782, filed Oct. 11, 2007, which claims the benefit of U.S. Provisional application Ser. No. 60/850,932, Filed Oct. 11, 2006, each of which is hereby incorporated by reference in its entirety, including all figures and tables.

BACKGROUND OF THE INVENTION

In addition to conventional bandages, adhesive means, compresses and the like which are applied with pressure directly against a bleeding open wound, considerable effort has been directed toward the development of chemical agents in various forms that accelerate or enhance the coagulation of blood flowing from an open wound to arrest blood flow. Many of these agents are in the "clotting chain," i.e., fibrinogen, thrombin, Factor VIII and the like. Others are based upon the use of collagens. Edwardson, in U.S. Pat. Nos. 5,763,411, 5,804,428, and 5,962,026, for example, teaches the use of fibrin in conjunction with a solid support and as an enzyme free sealant, and as a solid composition substantially free of catalytic enzymes.

Several patents disclose compositions that promote wound healing in conjunction with a clotting component, including Martin, U.S. Pat. Nos. 5,692,302, 5,874,479, and 5,981,606; Stillwell, U.S. Pat. No. 5,484,913, and Winter et al., U.S. Pat. No. 5,474,782. In U.S. Pat. No. 2,163,588, Cornish teaches a wound pad having very fine fibers carrying a viscous agent and a styptic for arresting and clotting blood flow. Eberl et al, U.S. Pat. No. 2,688,586, teach an improved hemostatic surgical dressing with alginic acid as a clotting agent. Masci et al., U.S. Pat. Nos. 2,772,999 and 2,773,000, also teach hemostatic surgical dressing including a pad and free acid cellulose glycolic acid. A patent for another hemostatic wound dressing is taught by Shelley in U.S. Pat. No. 3,206,361 having an active agent in the form of methylaminoacetocatechol hydrochloride. Likewise, Anderson, in U.S. Pat. No. 3,328,259, discloses a wound dressing containing a film of cellulose glycolic acid ether as the hemostatic agent.

A multitude of other patents, for example Sugitachi et al., U.S. Pat. No. 4,265,233, teach various ready-to-use bandages, pads or other carrying agents containing a hemostatic agents, including Factor VIII, fibrin, thrombin, collagen, polyethylene oxide, epsilon aminocaproic acid (EACA) with calcium chloride, etc. Sakamoto teaches in U.S. Pat. No. 4,655,211 a carrier in the shape of a flake or fiber having thrombin and Factor XIII affixed thereto.

Other patents disclose various fibers capable of inducing clotting. For example, Shimizu et al in U.S. Pat. No. 5,679,372 teaches absorbable acetocollagen fibers, while Bell, et al., U.S. Pat. No. 5,800,372, discloses a dressing made of microfibrillar collagen and a superabsorbant polymer for blood absorption and clotting inducement. U.S. Pat. No. 6,521,265 to Patterson and U.S. Pat. No. 6,187,347 to Patterson et al. disclose an admixture of salt ferrate with a cation exchange material that, when hydrated results in the concentration of blood and reduction of $Fe^{+6}$ to $Fe^{+++}$ to induce clotting.

Published U.S. application No. 20030008011 discloses acid forms of cross-linked polyacrylic acid with polyvinyl alcohol that forms a gel for stopping minor bleeding. Published U.S. application No. 20050137512 discloses a compressed sponge for hemorrhage control made by freeze drying a composition of polyacrylic acid.

BRIEF SUMMARY OF THE INVENTION

The subject invention pertains to materials and methods for stopping or decreasing blood flow from an open wound or a medical or surgical procedure site. Compositions of the invention comprise a salt or salts of one or more cross-linked hydrophilic polymer, such as a polyacrylic acid. In one embodiment, a composition of the invention comprises the sodium salt of crosslinked polyacrylic acid (CAS registration number # 9003-04-7). In an exemplified embodiment, a composition of the invention comprises sodium polyacrylate provided in a dry powdered form. A composition of the invention can be applied directly to a wound or treatment site, or it can be incorporated into a wound dressing, such as a bandage or fibrous material. The clot or scab formed at a wound site treated with the present invention is extremely elastic and exhibits considerable tensile strength when stretched to the breaking point. The subject invention also concerns wound and surgical site dressings and coverings, and methods of using a composition of the invention to stop blood flow from an open wound or treatment site.

BRIEF DESCRIPTION OF THE DRAWINGS

FIG. 1A shows the insertion of a sheath into the vascular access site. FIG. 1B shows the placing of a PCD around the sheath. FIG. 1C shows the filling of the PCD opening with QR powder. FIG. 1D shows the application of pressure over the powder with a standard gauze pad. FIG. 1E shows the pressure being released and the removal of the sheath. FIG. 1F shows the continuation of pressure for two minutes or until blood flow stops. Additional powder and pressure may be applied to control any leakage.

DETAILED DISCLOSURE OF THE INVENTION

Figure 1A:
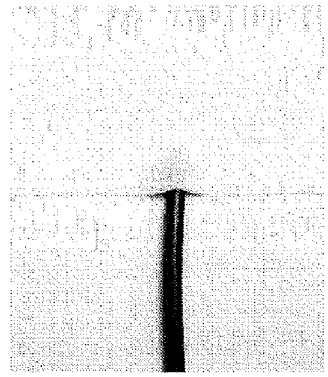
FIGS. 1A-1F show a containment device used with a composition of the invention ("QR powder") to control bleeding from a vascular access procedure.

The subject invention pertains to materials and methods for stopping or decreasing the blood flow from an open wound or a medical or surgical procedure site. Compositions of the invention comprise one or more cross-linked ionic hydrophilic polymers. Polymers contemplated within the scope of the invention include, but are not limited to, carboxyvinyl polymer such as polymethacrylic acid, and, biodegradable crosslinked sodium carboxymethylcellulose or similar derivatives, biodegradable crosslinked starches (for example, LYSORB, Archer Daniels Midland Corporation, Decatur, Ill.), guar gums, Arabic gums, karaya and other natural gums. Polyacrylic acid polymer comprises the structure:

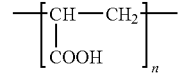

The salt form of a polyacrylic acid polymer comprises the structure:

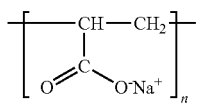

The salt form of polymers of the invention, such as polyacrylic acid, can be prepared from any suitable metal ion including, but not limited to, sodium, lithium, potassium, and calcium. Ammonium and triethanolamine salts of polyacrylate are also contemplated within the scope of the invention. In one embodiment, a polyacrylic acid is provided as sodium polyacrylate. In a specific embodiment, the sodium polyacrylic acid is that form described for CAS registration number 9003-04-7.

In one embodiment, cross-linked ionic polymers of the invention are super absorbing polymers (e.g., U.S. Pat. Nos. 5,525,703; 5,612,384; 5,461,085; 4,654,039; 3,670,731; 3,669,103; EP 0312952 and EP 0441507) or ionic hydrogels that can absorb and retain close to 20 times its own weight in water. Super absorbing polymers of the invention include, but are not limited to, polymers or copolymers of acrylic acid or methacrylic acid, or graft copolymers of acrylic acid and starch. This is to be differentiated by polyurethane hydrogels that can absorb but not retain (easily pushed out) the same amount of water. A hydrogel is a three-dimensional network of hydrophilic polymer chains that are crosslinked. The hydrogel is characterized by its extractables. A polyacrylic acid polymer of the invention preferably has percentage extractables in the range of from about 5% to about 30%. Extractables are the soluble components in the gel which include lightly crosslinked polymers. The linear or lightly crosslinked extractables can have a molecular weight in the range of 200,000 to 2 million. Particles of polyacrylic acid polymer can range in size from about 25 to about 1,000 microns. In an exemplified embodiment, a composition of the invention comprises sodium polyacrylate provided in a dry powdered form. The polyacrylate composition can be applied directly to a wound or treatment site, or it can be incorporated into a wound or surgical dressing, such as a bandage. The clot or scab formed at a wound or treatment site treated with the present invention is extremely elastic and exhibits considerable tensile strength when stretched to the breaking point.

Polymers of the invention also include superporous hydrogels (e.g., U.S. Pat. Nos. 6,271,278; 6,960,617; 7,056,957; and published U.S. application Nos. 20030008007; 20010038831; 200302332895; and 2004022402). Superporous hydrogels (for example, AQUAGEL, Akina, Inc, West Lafayette, Ind.) can be made from polyacrylic acid or polyacrylic acid copolymers. Superporous hydrogels of the invention include, but are not limited to, those of polyacrylamide, poly(sodium arcylate), poly(2-hydroxyethyl methacrylate), poly(hydroxypropyl methacrylate), poly(3-sulfopropyl acrylate, potassium salt), poly(2-acrylamido-2-methyl-1-propanesulfonic acid), poly({2-(acryloyloxy)ethyl}trimethyl sulfate). Poly(N-isopropyl acrylamide), poly(N-vinyl pyrrolidinone((PVP), modified sucrose, and gelatin. Superporous hydrogels are capable of holding 50 to 200 times their weight in water (Park (2002); Dorkoosh et al. (2002)).

Compositions of the present invention, including those compositions used in methods and dressings of the invention, can include, in addition to a salt of a hydrophilic polymer (e.g., sodium polyacrylate), a substantially anhydrous composition comprising a salt ferrate and/or a cation exchange material, such as, for example, a sulfonated ion exchange resin. A process for producing ferrates is taught in U.S. Pat. No. 4,545,974, the disclosure of which is incorporated herein by reference. In one embodiment, anhydrous compounds of the present invention comprise a monovalent, divalent, or trivalent salt ferrate ($M_2FeO_4$, $MFeO_4$ or $M_2(FeO_4)_3$, wherein M is a cation) and a cation exchange material. Cation exchangers contemplated within the scope of the invention include water insoluble polymers containing anionic functional groups such as —$SO_3^-$, —$OPO_3^-$, and —$COO^-$. In the practice of this invention, mixtures of insoluble polymers containing different anionic functional groups can be employed. The polymers can be cross-linked. For example, if the polymer is polystyrene, it can be cross-linked with 1% to 10% divinylbenzene. One embodiment of the present invention utilizes an ion exchange resin in the hydrogen ionic form of a sulfonated styrene divinylbenzene copolymer. Methods for preparing ion exchange resins of the invention are disclosed in U.S. Pat. No. 4,291,980, which was based, at least in part, on the production of spherical beads comprised of copolymer styrene and divinylbenzene as taught in U.S. Pat. Nos. 2,366,007 and 3,463,320. The counter ion in the ion-exchange resin can be any cation in the atomic table. The preferred counter-ions include hydrogen, elements in Groups IA and IIA. While the most preferred cation is hydrogen, mixed cations may be used such as hydrogen and a Group IA element and/or Group IIA element. In another embodiment, the cation-exchange material can be inorganic rather than organically based. Inorganic cation-exchange materials include, but are not limited to, natural or synthetic zeolites, hydrated alkali-aluminum silicates of the general formula $M_{2/n}O\cdot Al_2O_3\cdot ySiO_2\cdot wH_2O$ where M represents a group IA or IIA element, n is the cation valence, y is 2 or greater and w is the number of water molecules contained in the channels within the zeolite. In another embodiment, ion exchange celluloses may be used where the functionalities are classified as strong acid, intermediate acid or weak acid. In another embodiment, mixtures of organic based and inorganic based ion exchangers may be used.

Examples of elements which can be used as the cation in a salt ferrate of the invention include: H (hydrogen), Li (lithium), Na (sodium), K (potassium), Rb (Rubidium), Cs (Cesium), and Fr (Francium). In one embodiment, the salt ferrate used in a compound of the invention is potassium ferrate ($K_2FeO_4$). It is known in the art (see U.S. Pat. No. 4,545,974) that the decomposition by hydration of potassium ferrate produces the finest particles of iron oxide ($Fe_2O_3$) available through the following chemical reaction.

$$2K_2FeO_4 + 2H_2O \rightarrow 4K^+OH^- + Fe_2O_3 + \tfrac{3}{2}O_2 \uparrow \quad (I)$$

Compositions of the invention can comprise one or more different salt ferrates and in different amounts. For example, in one embodiment, a composition of the invention may comprise potassium ferrate and sodium ferrate in equal or different amounts.

Other cations and cationic groups that can be utilized in a salt ferrate of the present invention include:

TABLE I

| Be | Beryllium | Mg | Magnesium | Ca | Calcium |
|----|-----------|-----|-----------|-----|-----------|
| Sr | Strontium | Ba | Barium | Ra | Radium |
| Ti | Titanium | V | Vanadium | Cr | Chromium |
| Mn | Manganese | Fe | Iron | Co | Cobalt |
| Ni | Nickel | Cu | Copper | Zn | Zinc |
| Ga | Gallium | Ge | Geranium | Zr | Zirconium |

TABLE I-continued

| Nb | Niobium | Mo | Molybdenum | Tc | Technetium |
|---|---|---|---|---|---|
| Ru | Ruthenium | Rh | Rhodium | Pd | Palladium |
| Ag | Silver | Cd | Cadmium | In | Indium |
| Sn | Tin | Hf | Hafnium | Ta | Tantalum |
| W | Tungsten | Re | Rhenium | Os | Osmium |
| Ir | Iridium | Pt | Platinum | Au | Gold |
| Hg | Mercury | Tl | Thallium | Pb | Lead |
| Bi | Bismuth | Al | Aluminum | As | Arsenic |
| $NH_4$ | Cation | $N(C_4H_9)_4$ | Cation | | |

In those embodiments utilizing the $K_2FeO_4$ as the salt ferrate, or when the cation of the ferrate is H, Li, Na, Rb, Cs, or Fr, it can be understood from Equation I that hydroxide $(OH)^-$ radicals are produced. The hydroxide $(OH)^-$ radicals remain present in Equation I. It is the presence of the hydroxide $(OH)^-$ radicals that can cause a stinging, burning, or otherwise painful sensation when the composition is applied to a wound site. However, use of a salt ferrate having one of the cations listed in Table I produce a slightly altered chemical reaction which neutralizes all of the hydroxide ions produced. For example, using a calcium cation to replace the potassium cation in the salt ferrate, the following chemical reaction occurs:

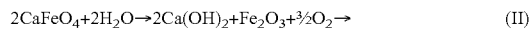

$$2CaFeO_4 + 2H_2O \rightarrow 2Ca(OH)_2 + Fe_2O_3 + \tfrac{3}{2}O_2 \rightarrow \qquad (II)$$

As can be observed from Equation II, the produced hydroxide ions are neutralized and combined with calcium. Very little free hydroxide anion is available because of the limited solubility of calcium hydroxide in water. Thus, in one embodiment, a salt ferrate compound of the subject invention utilizes one or more of the cations described in Table I.

Compositions of the subject invention can also comprise additional optional compounds or agents that provide for increased anti-microbial, absorptive, and/or wound healing properties. In one embodiment, a composition of the invention comprises a salt ferrate, a cationic exchange resin, and a silver compound. Silver compounds include, but are not limited to, silver metal (such as nano-silver); silver halides, such as silver chlorides, silver iodides, silver bromides, silver acetate, silver benzoate, silver nitrate, silver carbonate, silver laurate, etc.; silver oxides; silver sodium hydrogen zirconium phosphate; and silver/zinc form of Zeolite A.

Additional components of compositions of the present invention can include, for example, one or more of: zinc compounds, manganese compounds, calcium compounds, and/or copper compounds or derivatives thereof. Examples include, but are not limited to, zinc oxide, zinc sulfate, zinc stearate, manganese oxide, manganese sulfate, manganese citrate, calcium oxide, calcium sulfate, calcium citrate, calcium carbonate, cuprous sulfate; alginates, carrageenans, and agars; chitosan; absorption polymers such as cross-linked polyacylates and acylate copolymers; natural and/or synthetic gums, such as guar, arabic, or karaya; oxidized celluloses; starches, such as tapioca; and drugs, such as antifungal agents and antibiotics. Antibiotics contemplated include, but are not limited to, amikacin, gentamicin, kanamycin, neomycin, netilmicin, streptomycin, tobramycin, paromomycin, geldanamycin, herbimycin, loracarbef, ertapenem, imipenem/cilastatin, meropenem, cefadroxil, cefazolin, cefalotin/cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefdinir, cefepime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, prontosil (archaic), mafenide, sulfacetamide, sulfamethizole, sulfanilamide (archaic), sulfasalazine, sulfisoxazole, trimethoprim, trimethoprim-sulfamethoxazole (co-trimoxazole (TMP-SMX), demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, and tinidazole. Antifungal agents include, but are not limited to, natamycin, rimocidin, filipin, nystatin, amphotericin B, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, terbinafinem amorolfine, naftifine, butenafine, andulafungin, caspofungin, micafungin, ciclopirox, flucytosine, grisefulvin, gentian violet, haloprogin, tolnaftate, and undecylenic acid.

Compositions of the invention can be provided in any suitable form. In one embodiment, a composition of the invention is in a loose, free-flowing powder form. In another embodiment, a composition of the invention is provided in a solid wafer or tablet form. Wafers, tablets, and the like can be prepared using standard methods and materials known in the art. In one embodiment, a wafer or tablet is prepared by compressing a powder composition of the invention under substantial pressure, e.g., 1,000 to 50,000 lbs/in$^2$. In one embodiment, a wafer or tablet of the invention comprises a binder, such as Carbopol 974 NF. The use of suitable binders allows wafers and tablets to be prepared at lower pressures. The wafer or tablet can be applied directly to a wound or treatment site or the wafer or tablet can be broken up or crushed into smaller pieces or powder for application to a site. Wafers and tablets can be provided in bulk form or they can be individually packaged. Compositions of the invention are preferably stored under substantially anhydrous conditions and preferably applied as a dry dressing.

In one embodiment, a composition of the invention comprises:
I) a salt of cross-linked polyacrylic acid; and
II) a substantially anhydrous composition comprising:
a) a salt ferrate; and
b) a cation exchange material.

Compositions of the invention can comprise, for example, components I and II in a ratio of from about 20:1, or 10:1, or 9:1, or 8:1, or 7:1, or 6:1, or 5:1, or 4:1, or 3:1, or 2:1, or 1:1, by weight. In one embodiment, a composition of the invention comprises, for example, components "a" and "b" in a ratio of 1:10, or 1:9, or 1:8, or 1:7, or 1:6, or 1:5, or 1:4, or 1:3, or 1:2, or 1:1, or 1:0, by weight.

The subject invention also concerns methods of using a composition of the invention to stop blood flow from an open wound or surgical or medical treatment site. In one embodiment, a composition of the invention in dry powder form is applied directly to a wound from which blood or other bodily fluids are flowing. In one embodiment, a wound or treatment site treated with a composition of the invention is subsequently covered with a suitable wound covering or dressing. In another embodiment, a wound covering or dressing is impregnated or coated with or contains a composition of the invention and the covering or dressing is applied to the wound. Thus, the present invention can also be practiced in conjunction with wound coverings, dressings, and protective materials, such as bandages (such as BAND-AIDS), cotton gauze, absorptive pads, and the like. Examples of wound coverings, dressings, and protective materials contemplated for use in the subject invention include those described in U.S. Pat. Nos. 7,252,837; 7,112,714; 7,070,584; 7,030,288; 7,005,556; 6,936,746; 6,861,067; 6,787,682; 6,500,539; 6,399,092; 6,326,410; and 6,238,691.

The subject invention also concerns wound and surgical treatment site coverings, dressings, and the like. In one embodiment, a dressing of the invention comprises a pad that contains a composition of the invention within and/or on the surface of the pad. In a specific embodiment, the pad is composed of porous foam that is sufficiently open to allow a free flow of powder to fill the voids in the porous foam. The open voids can either be random (like a foam air conditioning filter) or organized into tunnels. The tunnels can keep compositions from mixing until needed. The tunnels can be round holes or geometric shapes. Around the perimeter of the randomly open foam a less porous border may be used to contain the composition. The pad can be designed so that lateral pressure can compress the foam or tunnels and hold the composition in place for inverted application. The foam can be made from polyurethane or other polymers.

In another embodiment, a dressing of the invention comprises a pad with fibers substantially perpendicularly oriented to the plane of the pad, wherein the fibers can hold and release a composition of the present invention. The dressing can be provided with or without an integrated foam or fabric or substrate backing. The dressing can be pre-loaded with a composition of the present invention. The dressing can be of a design wherein the fibers remain attached to the dressing during and/or after application to a wound or surgical site.

In one embodiment, a wound dressing of the invention comprises a flocked pad wherein the pad has a foam (e.g., polyurethane) portion and a flocked fibers portion. Flocking is a process of applying very short fibers onto a surface. In one embodiment, the foam portion is a porous foam as described above. In this embodiment, a composition of the invention can be loaded onto the side of the foam opposite that of the fibers and the composition can travel or flow through the foam and onto the fibers. The fibers can be attached to the foam portion and can be made, for example, out of calcium alginate. The fibers can be a woven or non-woven material. The fibers can be composed of any suitable material such as cotton, wool, etc. In one embodiment, the fibers are composed of a velvet fabric. The fibers can be coated or flocked with a composition of the present invention. Optionally, the fibers can be composed of dissolvable material (e.g., polyvinyl alcohol) or a biodegradable material (e.g., starch, calcium alginate, polysaccharides, etc.). In one embodiment, the fibers can be composed of a material that can dissolve in a solution, such as a saline solution. In another embodiment, the fibers themselves do not dissolve in solution but are attached to the pad portion via a substance or material that itself can dissolve in solution. This permits a solution to be contacted with a dressing of the invention that has been applied to a site where blood has coagulated and formed a scab, wherein the fibers dissolve or the attachment dissolves and the pad portion of the dressing can then be easily removed without ripping the scab off the wound.

Figure 1B:
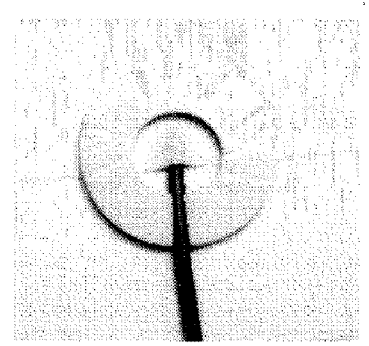
Figure 1C:
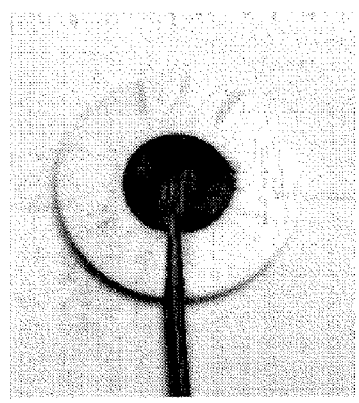
Figure 1D:
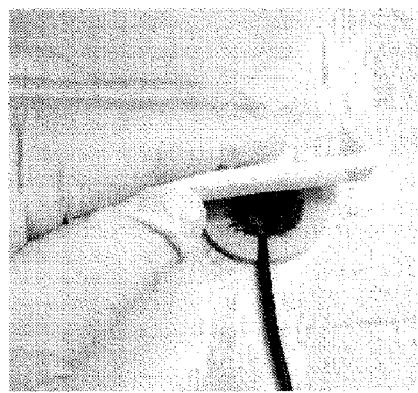
Figure 1E:
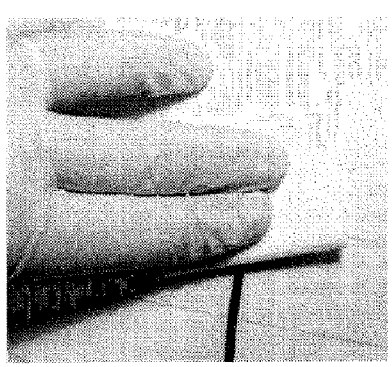
Figure 1F:
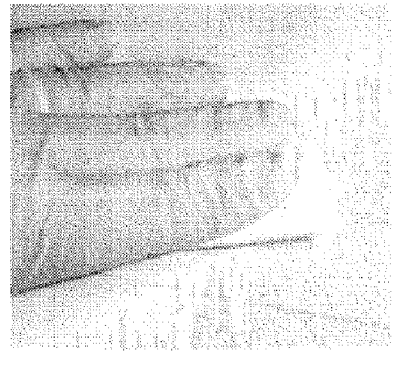

In another embodiment, a dressing of the invention comprises an "island" dressing wherein the dressing has a hollow or open center area that is positioned over the wound or medical treatment site and wherein a composition of the invention can be applied once the dressing is applied to the wound or treatment site. Alternatively, the dressing can have a composition of the invention pre-loaded into the center of the dressing prior to application to a wound or treatment site, wherein the composition is held in place in the dressing by a suitable material that can be removed prior to use of the dressing or that can dissolve in solution or upon contact with blood at the wound or treatment site. The island dressing can be of any suitable size, and shape, and thickness appropriate for the wound site or medical procedure being performed. Preferably, the hollow center portion of the dressings where the composition of the invention is to be applied is larger in diameter and/or circumference than the wound site or procedural site being treated. The dressing can be circular, oval, square, rectangular, diamond, trapezoid, triangular, or any other shape, including irregular shapes. The dressing can be composed of any suitable material including, but not limited to, foam, cork, plastic, woven fiber, compressed cotton, and paper materials. One embodiment of an island dressing of the present invention is shown in FIGS. 1A-1F being used for controlling bleeding during a vascular access procedure on a patient.

In another embodiment, a dressing of the invention comprises a pouch or other container that contains a composition of the invention and wherein at least one surface of the pouch or container that contacts the wound or treatment site is dissolvable or biodegradable in blood, bodily fluids, exudates, or other liquids or solvents. In one embodiment, a pouch can be composed of paper or paper blends, polypropylene, or polyvinyl alcohol.

In a further embodiment, a composition of the invention is provided in a paste formulation. Carriers that can be used in a paste of the invention include long chain hydrocarbons that impart body, such as, for example, mineral oil and petroleum jelly.

The subject invention also concerns kits comprising in one or more containers or packages a polyacrylate composition of the present invention. In a specific embodiment, a kit comprises a composition comprising a sodium salt of cross-linked polyacrylate. Kits can also comprise one or more different salt ferrates of the invention, and/or a cationic exchange resin, and/or silver compound as described herein. In addition to the foregoing, kits of the invention can also include additional components, including for example, one or more of: zinc compounds, manganese compounds, calcium compounds, and/or copper compounds or derivatives thereof. Examples include, but are not limited to, zinc oxide, zinc sulfate, zinc stearate, manganese oxide, manganese sulfate, manganese citrate, calcium oxide, calcium sulfate, calcium citrate, calcium carbonate, cuprous sulfate; alginates, carrageenans, and agars; chitosan; absorption polymers such as cross-linked polyacylates and acylate copolymers; natural and/or synthetic gums, such as guar, arabic, or karaya; oxidized celluloses; starches, such as tapioca; and drugs, such as antibiotics. In one embodiment, a composition of the invention is packaged in a container that is designed in a manner so as to preserve the anhydrous nature of the composition until the container is opened. A kit of the present invention can also comprise a wound covering, dressing, or other wound or surgical site protective material, preferably provided and maintained in sterile form until the package or container is opened for use.

The methods and compositions of the present invention can be used in the treatment of humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

The dosage or amount of a composition of the invention to be typically administered or applied to a site can be readily determined by an ordinarily skilled clinician and will be dependent on various factors, such as the size and type of wound or the surgical or medical procedure being performed, the amount of blood or fluid present in the wound or treatment site, and physical characteristics of the patient, as well as other drugs or treatments the patient is receiving.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Blood Seal Test

One tenth (0.1) of a milliliter of stabilized bovine blood was spread out evenly on a one inch diameter circular template in a plastic tray. 300 mg of test powder was poured onto the template to cover the circular area. Powder tested included QR hemostatic powder ("QUICK RELIEF", Biolife, L.L.C., Sarasota, Fla.) composed of a mixture of 1 part of potassium ferrate to 7 parts of a 2% crosslinked, hydrogen form of polystyrene resin functionalized with sulfonic acid only, cross-linked sodium salt of polyacrylic acid only (CABLOC 3050F), a mixture of QR and CABLOC 3050F in various ratios. After 90 seconds, the integrity of the seal (barrier) formed by the blood and test powder was evaluated by scraping with a small spatula. The amount of seal remaining after scraping was measured. Qualitative readings of the following parameters were made: blood absorption, adhesion of the seal during the scrapping process and % coverage of the seal after scrapping. In the case of adhesion, an excellent rating is one in which the scab cannot be scrapped off with moderate force. A poor rating is one in which the scab can be scrapped very easily with little force.

TABLE 1

1.5 Minute Blood Seal Test

| sample | QR | 10% SAP, 90% QR | 20% SAP, 80% QR |
|---|---|---|---|
| blood absorption | fair | fair | good |
| mg remaining seal | 15.2, 13.6, 15.1 | 11.6, 13.5, 15.9, | 36.3, 26.0, 28.6 |
| % coverage | 20, 20, 15 | 10, 15, 25 | 40, 35, 35 |
| adhesion | fair | fair | excellent |
| remaining seal after 30 min | brittle, easy to scrap off | brittle, easy to scrap off | less brittle, not all scrapped off |
| sample | 30% SAP, 70% QR | 40% SAP, 60% QR | 50% SAP, 50% QR |
| blood absorption | very good | excellent | excellent |
| mg remaining seal | 40.4, 50.5, 42.0 | 58.6, 55.7, 56.5 | 67.4, 56.7, 55.6 |
| % coverage | 45, 60, 65 | 65, 60, 65 | 55, 55, 65 |
| adhesion | excellent | excellent | excellent |
| remaining seal after 30 min | strong, not scrapped off | strong, not scrapped off | strong, not scrapped off |
| sample | 60% SAP, 40% QR | 70% SAP, 30% QR | 80% SAP, 20% QR |
| blood absorption | excellent | excellent | excellent |
| mg remaining seal | 85, 67.4, 70.8 | 22.4, 11.6, 15.3 | 5.6, 5.0, 6.7 |
| % coverage | 70, 80, 55 | 50, 50, 50 | 40, 25, 35 |
| adhesion | excellent | very good | very good |
| remaining seal after 30 min | strong, not scrapped off | brittle, easy to scrap due to thin remaining seal | brittle, easy to scrap due to thin remaining seal |
| sample | 90% SAP, 10% QR | 100% SAP | |
| blood absorption | excellent | excellent | |
| mg remaining seal | 3.1, 1.2, 2.5 | 2.6, 5.2, 3.4 | |
| % coverage | 0, 0, 0 | 0, 0, 0 | |
| adhesion | moderate | moderate | |
| remaining seal after 30 min | NA | NA | |

Notes:
NA denotes not applicable.
Mg remaining seal is a qualitative measure of seal thickness; thickness increases as mg of remaining seal increases.

Definitions and Sources of Materials

The term "SAP" denotes a super absorbing polymer of crosslinked, high molecular weight, partially neutralized (sodium salt) polyacrylic acid. SAP has been known for many years as a super absorbent material used in diapers and feminine hygiene products. The SAP under study was CABLOC 3050F from DeGussa (Dusseldorf, Germany). It is a white powder. It has an average particle size of 150 microns. The CAS number is 9003-04-7.

The term "QR" denotes a commercial hemostatic powder ("QUICK RELIEF") composed of a mixture of 1 part of potassium ferrate to 7 parts of a 2% crosslinked, hydrogen form of polystyrene resin functionalized with sulfonic acid (available from Biolife L.L.C. Sarasota, Fla.).

Blood Seal Test—One tenth (0.1) of a milliliter of stabilized bovine blood was spread out evenly on a one inch diameter circular template in a plastic tray. 300 mg of test powder was poured onto the template to cover the circular area. Powder tested included QR only, cross-linked sodium salt of polyacrylic acid only (CABLOC 3050F), a mixture of QR and CABLOC 3050F in various ratios. After 90 seconds, the integrity of the seal (barrier) formed by the blood and test powder was evaluated by scraping with a small spatula. The amount of seal remaining after scraping was measured. Qualitative readings of the following parameters were made: blood absorption, adhesion of the seal during the scrapping process and % coverage of the seal after scrapping.

Results

QR powder absorbed a fair amount of blood and formed a thin seal with initially fair adhesion. The remaining QR seal became very brittle on standing and could be scrapped off very easily from the plastic tray after half an hour. CABLOC 3050F (Degussa AG, Dusseldorf, Germany) (SAP) by itself absorb blood extremely well and formed a very sticky, gummy blood seal which adhered moderately. However, the gummy blood seal could be scrapped off with moderate force leaving no remaining seal. The lifted seal was strong cohesively and was very elastic. At 10% addition of (SAP) in QR, there was little or no change to the blood seal properties of QR. As increasing amount of SAP (20 to 30%) was added to QR, blood absorption, adhesion, % coverage and mg of remaining seal improved. At 40% to 60% SAP addition levels, blood absorption and adhesion were excellent, the mg of remaining seal was very high compared to QR or SAP separately by themselves. Furthermore, blood absorption was excellent, % coverage of the remaining seal was 50 to 85%, and after 30 minutes, the remaining seals were strong and elastomeric, and were not scrapped off easily with the spatula. At 70% SAP addition, blood absorption was excellent, % coverage was lower at 50%, mg of remaining seal was significantly reduced and after 30 minutes, the remaining seal was brittle and easily scrapped off. At 80% SAP addition, blood absorption was excellent, % coverage and mg of remaining seal decreased substantially although adhesion was still very good. After 30 minutes, the remaining seal was brittle and easy to scrap off. At 90% SAP addition, blood absorption was excellent, % coverage was zero, the mg of remaining seal was very low and adhesion was moderate.

In previous work, it has been shown that QR has excellent in vitro antimicrobial and oxidizing properties. SAP is not known to be antimicrobial or oxidizing. Thus, the combination of QR and SAP gives surprising and desirable properties to a hemostatic dressing not achieved by QR by itself or SAP by itself. The seal formed from the combined QR and SAP material is more easily removed by wetting with water or saline than that of the QR seal.

EXAMPLE 2

Blood Seal Test at Longer Period of Standing

The blood seal test described in Example 1 was followed except that the time of standing was changed to 180 seconds from 90 seconds. The results are summarized in Table 2.

TABLE 2

Three Minute Blood Seal Test

| sample | QR | 10% SAP, 90% QR | 20% SAP, 80% QR |
|---|---|---|---|
| blood absorption | very good | excellent | excellent |
| mg remaining seal | 21 | 29.6 | 35.6 |
| % coverage | 60 | 65 | 80 |
| adhesion | very good | excellent | excellent |
| remaining seal after 30 min | brittle, easy to scrap off | brittle, moderately easy to scrap off | brittle, moderately easy to scrap off |
| sample | 30% SAP, 70% QR | 40% SAP, 60% QR | 50% SAP, 50% QR |
| blood absorption | excellent | excellent | excellent |
| mg remaining seal | 41.6 | 52.8 | 73.2 |
| % coverage | 80 | 90 | 95 |
| adhesion | excellent | excellent | excellent |
| remaining seal after 30 min | moderately brittle, moderately easy to scrap off | moderately brittle, moderately easy to scrap off | strong, hard to scrap off |
| sample | 60% SAP, 40% QR | 70% SAP, 30% QR | 80% SAP, 20% QR |
| blood absorption | excellent | excellent | excellent |
| mg remaining seal | 95.1 | 14.2 | 2.5 |
| % coverage | 95 | 30 | 0 |
| adhesion | excellent | good | moderate |

TABLE 2-continued

Three Minute Blood Seal Test

| remaining seal after 30 min | strong, hard to scrap off | moderately easy to scrap off | moderately easy to scrap off |
|---|---|---|---|
| sample | 90% SAP, 10% QR | 100% SAP | |
| blood absorption | excellent | excellent | |
| mg remaining seal | 2.6 | 2.1 | |
| % coverage | 0 | 0 | |
| adhesion | moderate | moderate | |
| remaining seal after 30 min | NA | NA | |

Notes:
NA denotes not applicable.
Mg remaining seal is a qualitative measure of seal thickness; thickness increases as mg of remaining seal increases.

The trends shown in the three minute blood seal test were similar to that of the 1.5 minute test. Mixtures of QR and SAP particularly those containing 40 to 60% of SAP gave hemostatic properties that were surprisingly better than either QR or SAP by themselves.

EXAMPLE 3

Test of Composition on a Patient Comprising QR/SAP in a 1:4 Ratio

A two inch by two inch area of patient's arm was shaved and cleaned with rubbing alcohol. A one inch circle was marked on this area. A blood sample was obtained from the patient's finger using an auto-Lancet. The blood was spread over the one inch circle. A QR/SAP mixture in a 1:4 ratio (containing 80% SAP) was sprinkled over the blood. The mixture and blood formed a very adhesive seal on the skin. It was difficult to pry the seal open from the skin. The top showed a white patch that looked like a dressing without the use of a bandage. A piece of seal taken off was viewed at 10× to 40× magnification under a microscope; the seal looked like a fairly continuous matrix. The seal was wetted with water, the top layer of mixture including the expanded SAP was removed leaving a thin layer of tightly adhered seal still intact. After removing the seal after several water flashing, the spot was finally cleaned with 5% CHLOROX bleach.

EXAMPLE 4

In Vitro Hemostasis Test

The In Vitro Hemostasis Test Apparatus was used to evaluate the efficiency to control bleeding of hemostatic dressings. The test provides a measure of seal strength as defined by the blood pressure at which a dressing fails. The apparatus consists of a pump forcing blood up a column to provide a constant head pressure at the point of the Test Block which has a ½" hole drilled into it. The height of the column of blood vs. the Test Block height is proportional to the pressure at the outlet of the test block. Bovine blood is allowed to flow to the surface of the block and the blood is spread evenly over the outlet hole. One gram of test powder was poured into the blood and blood was then allowed to pressurize thru the seal after a specified standing period. The pressure at which the seal fails is recorded. Three compositions were tested: QR powder, SAP powder and a 1:1 mixture of QR and SAP. The results are shown below:

TABLE 3

In Vitro Hemostasis Test

| Test Dressing | Failure Pressure (mm Hg) |
|---|---|
| QR | 107 |
| SAP | No seal formed |
| 1:1 mix of QR and SAP | 396 |

In this test, SAP did not form a seal, whereas QR formed a seal that broke at 107 mm Hg. Surprisingly, the mixture of QR and SAP formed a much stronger seal that failed at 396 mm Hg.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 5,763,411
U.S. Pat. No. 5,804,428
U.S. Pat. No. 5,962,026
U.S. Pat. No. 5,692,302
U.S. Pat. No. 5,874,479
U.S. Pat. No. 5,981,606
U.S. Pat. No. 5,484,913
U.S. Pat. No. 5,474,782
U.S. Pat. No. 2,163,588
U.S. Pat. No. 2,688,586
U.S. Pat. No. 2,772,999
U.S. Pat. No. 2,773,000
U.S. Pat. No. 3,206,361
U.S. Pat. No. 3,328,259
U.S. Pat. No. 4,265,233
U.S. Pat. No. 4,655,211
U.S. Pat. No. 5,679,372
U.S. Pat. No. 5,800,372
U.S. Pat. No. 6,521,265
U.S. Pat. No. 6,187,347
U.S. Pat. No. 4,545,974
U.S. Pat. No. 4,291,98

U.S. Pat. No. 2,366,007
U.S. Pat. No. 3,463,320
U.S. Pat. No. 7,252,837
U.S. Pat. No. 7,112,714
U.S. Pat. No. 7,070,584
U.S. Pat. No. 7,030,288
U.S. Pat. No. 7,005,556
U.S. Pat. No. 6,936,746
U.S. Pat. No. 6,861,067
U.S. Pat. No. 6,787,682
U.S. Pat. No. 6,500,539
U.S. Pat. No. 6,399,092
U.S. Pat. No. 6,326,410
U.S. Pat. No. 6,238,691
U.S. Pat. No. 6,271,278
U.S. Pat. No. 6,960,617
U.S. Pat. No. 7,056,957
U.S. Pat. No. 5,525,703
U.S. Pat. No. 5,612,384
U.S. Pat. No. 5,461,085
U.S. Pat. No. 4,654,039
U.S. Pat. No. 3,670,731
U.S. Pat. No. 3,669,103
U.S. Pat. No. 5,750,585
U.S. Published Application No. 20030008011
U.S. Published Application No. 20050137512
U.S. Published Application No. 20030008007
U.S. Published Application No. 20010038831
U.S. Published Application No. 200302332895
U.S. Published Application No. 2004022402
EP 0312952
EP 0441507
Dorkoosh F. A. et al., (2002), "Evaluation of superporous hydrogel and composite in porcine intestine ex-vivo", *Eur J Pharm Biopharm*, 53: 161-166.
Park, K., July/August 92002), "Superporous Hydrogels for Pharmaceutical & Other Applications", *Drug Delivery Technologies, Vol.* 2, No. 5.
Chen et al. (1999) *Journal of Biomedical Material Research*, 44:53-62.
Drews et al. (1999) Quest of Tomorrow's Medicines, New York, Springer-Verlag.
Wichterle et al. (1960) *Nature*, Vol. 185: 117-118
Chen et al. (2000) *J. Controlled Rel*. Vol. 64: 39-51
Shalaby et al. (1992) *Biomaterials, Vol.* 13; 289-296
Dorkoosh F. A. et al., (2001) *J. Controlled Rel*. Vol. 71: 307-318
Dorkoosh F. A. et al. *Pharm. Sci* (in press)
Dorkoosh F. A. et al. *Pharm. Res*. (in press)
Chang et al. (2000) *Pharm Technol*. Vol. 24(6): 52
Ciceri et al. (2002) *Paper 106 presented at 37th Annual Meeting of the American Society of Neuroradiology*, April 2-8.

We claim:

1. A method for stopping or decreasing the flow of blood from an open wound or surgical or medical treatment site, said method comprising applying to said wound or surgical or medical treatment site an effective amount of a composition comprising:
   i) one or more cross-linked hydrophilic polymers; and
   ii) a substantially anhydrous composition comprising:
      a) a salt ferrate; and, optionally,
      b) a cation exchange material; and/or
      c) an agent that provides for anti-microbial, absorptive, and/or wound healing properties;
   wherein said composition comprises said cross-linked hydrophilic polymers and said substantially anhydrous composition in a ratio of from 50:50 to 60:40;
   whereby the flow of blood from said wound or surgical or medical treatment site is stopped or decreased.

2. The method according to claim 1, wherein said cross-linked hydrophilic polymer is a super absorbing polymer.

3. The method according to claim 1, wherein said cross-linked hydrophilic polymer is a polyacrylic acid.

4. The method according to claim 1, wherein said cross-linked hydrophilic polymer is a superporous hydrogel.

5. The method according to claim 4, wherein said superporous hydrogel is polyacrylamide, poly(sodium acrylate), poly(2-hydroxyethyl methacrylate), poly(hydroxypropyl methacrylate), poly(3-sulfopropyl acrylate, potassium salt), poly(2-acrylamido-2-methyl-1-propanesulfonic acid), poly({2-(acryloyloxy)ethyl}trimethyl sulfate), Poly(N-isopropyl acrylamide), poly(N-vinyl pyrrolidinone((PVP)), modified sucrose, or gelatin.

6. The method according to claim 1, wherein said cross-linked hydrophilic polymer is a carboxymethylcellulose polymer, a starch, a guar gum, an Arabic gum, or other natural gums.

7. The method according to claim 1, wherein said composition further comprises a cation exchange material.

8. The method according to claim 1, wherein said composition further comprises one or more of a zinc compound, a manganese compound, a calcium compound, or a copper compound, or an alginate, a carrageenan, an agar, chitosan, absorption polymers, a gum, an oxidized cellulose, a starch, or a drug.

9. The method according to claim 8, wherein the drug is an antifungal agent or an antibiotic.

10. The method according to claim 1, wherein said salt ferrate comprises a lithium, sodium, potassium, rubidium, cesium, or francium cation.

11. The method according to claim 1, wherein said salt ferrate comprises a beryllium, strontium, titanium, manganese, nickel, gallium, niobium, ruthenium, silver, tin, tungsten, iridium, mercury, bismuth, ammonium ($NH_4$) cation, magnesium, barium, vanadium, iron, $N(C_4H_9)_4$ cation, geranium, molybdenum, rhodium, cadmium, hafnium, rhenium, Platinum, thallium, aluminum, copper, calcium, radium, chromium, cobalt, zinc, zirconium, arsenic, palladium, indium, tantalum, osmium, gold, lead, or technetium cation.

12. The method according to claim 1, wherein said cationic exchange material comprises a water insoluble polymer containing an anionic functional group.

13. The method according to claim 12, wherein said anionic functional group is selected from the group consisting of —$SO_3^-$, —$OPO_3^-$, and —$COO^-$.

14. The method according to claim 1, wherein said cation exchange material is a water insoluble polymer that is cross-linked.

15. The method according to claim 1, wherein said cation exchange material is a hydrogen ionic form of sulfonated styrene divinylbenzene copolymer.

16. The method according to claim 1, wherein said one or more cross-linked hydrophilic polymers is provided as a salt in said composition.

17. The method according to claim 1, wherein said one or more cross-linked hydrophilic polymers is a salt of polyacrylate in dry powder form.

18. The method according to claim 17, wherein said salt of polyacrylate is sodium polyacrylate.

19. The method according to claim 1, wherein said wound or surgical or medical treatment site is on a human, dog, cat, rabbit, ferret, guinea pig, hamster, pig, monkey, gerbil, horse, mule, donkey, burro, cow, sheep, alligator, lion, tiger, bear, camel, giraffe, hippopotamus, or rhinoceros.

20. The method according to claim 1, wherein said method enhances the formation of a clot or scab at said site.

21. The method according to claim 1, wherein the ratio, by weight, of said one or more cross-linked hydrophilic polymers and said substantially anhydrous composition is about 1:1.

22. The method according to claim 1, wherein said substantially anhydrous composition comprises potassium ferrate.

23. The method according to claim 1, wherein said one or more cross-linked hydrophilic polymers is a cross-linked ionic hydrophilic polymer.

24. A method for providing a clot or scab at a wound or surgical or medical treatment site, said method comprising applying to said wound or surgical or medical treatment site an effective amount of a composition comprising:
   i) one or more cross-linked hydrophilic polymers; and
   ii) a substantially anhydrous composition comprising:
      d) a salt ferrate; and, optionally,
      e) a cation exchange material; and/or
      f) an agent that provides for anti-microbial, absorptive, and/or wound healing properties;
   wherein said composition comprises said cross-linked hydrophilic polymers and said substantially anhydrous composition in a ratio of from 50:50 to 60:40:
   whereby a clot or scab is formed at said wound or surgical or medical treatment site.

25. The method according to claim 24, wherein the ratio, by weight, of said one or more cross-linked hydrophilic polymers and said substantially anhydrous composition is about 1:1.

26. The method according to claim 24, wherein said substantially anhydrous composition comprises potassium ferrate.

27. The method according to claim 24, wherein said one or more cross-linked hydrophilic polymers is a salt of polyacrylate in dry powder form.

28. The method according to claim 27, wherein said salt of polyacrylate is sodium polyacrylate.

29. The method according to claim 24, wherein said one or more cross-linked hydrophilic polymers is a cross-linked ionic hydrophilic polymer.

* * * * *

UNITED STATES PATENT AND TRADEMARK OFFICE
CERTIFICATE OF CORRECTION

PATENT NO. : 8,361,504 B2
APPLICATION NO. : 12/421300
DATED : January 29, 2013
INVENTOR(S) : John Hen et al.

Page 1 of 1

It is certified that error appears in the above-identified patent and that said Letters Patent is hereby corrected as shown below:

Column 5,
Line 26, "$2CaFeO_4 + 2H_2O \rightarrow 2Ca(OH)_2 + Fe_2O_3 + {}^3/_2O_2 \rightarrow$"

should read

--$2CaFeO_4 + 2H_2O \rightarrow 2Ca(OH)_2 + Fe_2O_3 + {}^3/_2O_2 \uparrow$--.

Signed and Sealed this
Twenty-third Day of April, 2013

Teresa Stanek Rea
*Acting Director of the United States Patent and Trademark Office*